United States Patent
Geese

(10) Patent No.: US 8,495,919 B1
(45) Date of Patent: Jul. 30, 2013

(54) TEST APPARATUS AND METHOD FOR DETERMINING AT LEAST ONE CHARACTERISTIC OF A PLURALITY OF TEST SPECIMENS

(75) Inventor: Douglas A. Geese, Churubusco, IN (US)

(73) Assignee: Fort Wayne Metals Research Products Corporation, Fort Wayne, IN (US)

( * ) Notice: Subject to any disclaimer, the term of this patent is extended or adjusted under 35 U.S.C. 154(b) by 782 days.

(21) Appl. No.: 12/722,998

(22) Filed: Mar. 12, 2010

Related U.S. Application Data

(63) Continuation-in-part of application No. 12/560,541, filed on Sep. 16, 2009, now abandoned.

(60) Provisional application No. 61/098,269, filed on Sep. 19, 2008.

(51) Int. Cl.
*G01N 3/20* (2006.01)
*G01N 25/00* (2006.01)

(52) U.S. Cl.
USPC ............................................. 73/849; 374/52

(58) Field of Classification Search
USPC ............................................. 73/849; 374/52
See application file for complete search history.

(56) References Cited

U.S. PATENT DOCUMENTS

| | | | |
|---|---|---|---|
| 4,300,398 A * | 11/1981 | Kaltenekker et al. | 73/849 |
| 4,805,679 A * | 2/1989 | Czinner | 73/849 X |
| 4,860,040 A | 8/1989 | Tamamura et al. | |
| 5,101,667 A * | 4/1992 | Tidiere et al. | 73/849 |
| 5,163,330 A * | 11/1992 | Tidiere et al. | 73/849 |
| 5,508,200 A | 4/1996 | Tiffany et al. | |
| 6,168,571 B1 | 1/2001 | Solar et al. | |
| 7,036,364 B2 * | 5/2006 | Swillo et al. | 73/849 X |
| 7,139,083 B2 | 11/2006 | Fielden et al. | |
| 7,196,782 B2 | 3/2007 | Fielden et al. | |
| 7,278,323 B2 * | 10/2007 | Hartmann et al. | 73/849 X |
| 7,297,070 B2 * | 11/2007 | Ashida et al. | 73/849 X |
| 7,349,090 B2 | 3/2008 | Wack et al. | |
| 7,882,748 B2 * | 2/2011 | Wen et al. | 73/849 |
| 8,176,792 B2 * | 5/2012 | Kozasa et al. | 73/849 X |
| 2007/0015289 A1 | 1/2007 | Kao et al. | |
| 2007/0186642 A1 * | 8/2007 | Sano et al. | 73/172 |

(Continued)

FOREIGN PATENT DOCUMENTS

WO WO2006/104823 A2 10/2006

OTHER PUBLICATIONS

Brochure—Shapetrack Nitonol Transformation Temperature Test System, confirmd, but by Sep. 19, 2008, 1 page.

(Continued)

*Primary Examiner* — Thomas P Noland
(74) *Attorney, Agent, or Firm* — Faegre Baker Daniels LLP

(57) ABSTRACT

A test apparatus and method for determining at least one characteristic of a test specimen. An exemplary test specimen is a shape memory metal alloy and an exemplary characteristic is a transformation temperature of the shape memory metal alloy. The test apparatus may include a chiller unit including a tank containing a chilling medium, such as isopropyl alcohol or denatured alcohol, which holds a removable fixture tray that can accommodate up to ten specimens, or more. The fixture tray holds the test specimens in an initial deformed condition, and the cooling medium may be gradually heated to induce transformation of the specimens. The test apparatus may include a vision-based optical system which includes a camera that tracks the specimens within its field of view.

27 Claims, 10 Drawing Sheets

U.S. PATENT DOCUMENTS

| | | | |
|---|---|---|---|
| 2008/0053577 A1 | 3/2008 | Syed et al. | |
| 2008/0215131 A1 | 9/2008 | Magnuson et al. | |
| 2009/0084190 A1* | 4/2009 | Sugahara | 73/849 |
| 2009/0272198 A1* | 11/2009 | Wen et al. | 73/849 |
| 2012/0067134 A1* | 3/2012 | Bell et al. | 73/849 X |

OTHER PUBLICATIONS

Article—Fatigue Performance of Nitinol Round Wire with Varying Cold Work Reductions, Jeremy E. Schaffer et al., Fort Wayne Metals Research Products Corporation, but by Sep. 19, 2008, 12 pages.

Article—Standard Test Method for Determination of Transformation Temperature of Nickel-Titanium Shape Memory Alloys by Bend and Free Recovery, ASTM International Designation: F2082-06, Aug. 2006, pp. 11-7.

Article—Uchil, Jayagopal, "Shape Memory Alloys—Characterization Techniques," Pramana—Journal of Physics, vol. 58, Nos. 5 & 6, pp. 1131-1139, May and Jun. 2002.

Article Lehnert, T. et al. "Transformation Properties and Microstructure of Sputter-Deposited Ni-Ti Shape Memory Alloy Thin Films." Journal of Materials Science 37, pp. 1523-1533, (2002).

Article Poncet et al. "Manufacture of Nitinol Tube", Memry Corporation, May 2006, 6 pages.

Article—Wu, Ming H.,"Fabrication of Nitinol Materials and Components" Proceedings of the International Conference on Shape Memory and Superelastic Technologies, Kunming, China, pp. 285-292, (2001).

* cited by examiner

TEST APPARATUS AND METHOD FOR DETERMINING AT LEAST ONE CHARACTERISTIC OF A PLURALITY OF TEST SPECIMENS

RELATED APPLICATIONS

This application is a continuation-in-part of U.S. patent application Ser. No. 12/560,541, filed Sep. 16, 2009, and claims the benefit of U.S. Provisional Patent Application Ser. No. 61/098,269, filed Sep. 19, 2008, the entire disclosures of which are expressly incorporated by reference herein.

BACKGROUND OF THE INVENTION

1. Field of the Invention

The present invention relates to a test apparatus and method for determining at least one characteristic of a test specimen, and in one application, relates to a test apparatus and method for determining a transformation temperature of a shape memory metal alloy. An exemplary application is a test apparatus and method for determining the martensite-to-austenite transformation temperatures of nickel titanium alloys.

2. Description of the Related Art

ASTM Method F2082 is a test method for the determination of transformation temperatures of nickel titanium shape memory metal alloys by bend and free recovery. This test method involves cooling a test specimen to its nominally fully martensite phase, deforming the specimen, and heating the specimen to its fully austenite phase. During heating, the motion of specimen is measured and is plotted versus specimen temperature for determining the martensite-to-austenite transformation temperatures.

A test apparatus for carrying out this method is contemplated in ASTM Standard F2082, and generally includes a fixture in which a specimen is held, the fixture submerged in a cooling bath. The specimen is deformed in the bath, and placed on the fixture which holds the specimen so as to not interfere with the free recovery of the specimen on heating. The bath is heated, and a thermocouple is used to measure the temperature of the bath. A transducer is used to detect the change in shape of the specimen as the specimen straightens, and displacement and temperature are measured and plotted versus one another to determine physical characteristics of the specimen, such as the martensite-to-austenite transformation temperature.

One known test device for implementing ASTM Standard F2082 is the Shape Track™ device, available from Confirmd LLC of San Carlos, Calif., and is similar to the test apparatus contemplated by ASTM Standard F2082. This device is based on the use of a linear variable differential transducer (LVDT) which is placed in contact with the test specimen to measure displacement. However, it is thought that contact of the transducer with the specimen could adversely affect the accuracy of the test data. Also, liquid nitrogen is used to cool the bath, which can be both hazardous and costly. Further, the bath temperature is not accurately controlled per the ASTM specification, as a hotplate is used, which cannot provide uniform and consistent temperature changes. Finally, this apparatus can only test one specimen at a time.

What is needed is a test apparatus and method for determining transformation temperatures of shape memory metal alloys which is an improvement over the foregoing.

SUMMARY OF THE INVENTION

In an exemplary embodiment of the present disclosure, a test apparatus for monitoring at least one characteristic of a test specimen is provided. The test apparatus may test the test specimen in a non-contact method while the test specimen is submerged in a bath. The test apparatus may test multiple test specimens at the same time.

In another exemplary embodiment of the present disclosure, a method for monitoring at least one characteristic of a test specimen is provided. The method may be a non-contact method for monitoring the test specimen while the test specimen is submerged in a bath. The method may test multiple test specimens at the same time.

In a further exemplary embodiment of the present disclosure, a method for testing at least one characteristic of a plurality of test specimens is provided. The plurality of test specimens being shape memory alloys, The method comprising the steps of: supporting the plurality of test specimens on a fixture in a spaced apart relationship; positioning the plurality of test specimens within a liquid bath; setting the temperature of the liquid bath at a first temperature; altering a shape of each of the plurality of test specimens while positioned in the liquid bath; capturing at least one image of each of the plurality of test specimens within the liquid bath when the liquid bath is at the first temperature; changing the temperature of the liquid bath to a second temperature; capturing at least one image of each of the plurality of test specimens within the liquid bath when the liquid bath is at the second temperature; and determining the at least one characteristic of the plurality of test specimens based on the images of the plurality of test specimens. In one example, the fixture includes a plurality of mandrels and the step of altering the shape of each of the plurality of test specimens while positioned in the liquid bath includes the step of bending each of the plurality of test specimens against a respective one of the plurality of mandrels. In another example, the method further comprises the steps of: positioning a camera above the plurality of test specimens; while the liquid bath is at the first temperature, moving the camera such that each of the plurality of test specimens is within a field of view of the camera. The plurality of test specimens including a first test specimen and a second test specimen. The camera being moved to a first position to bring the first specimen within the field of view of the camera and being moved to a second position to bring the second specimen within the field of view of the camera. The method further comprising the step of while the liquid bath is at the second temperature, moving the camera such that each of the plurality of test specimens is within a field of view of the camera. The camera being moved to the first position to bring the first specimen within the field of view of the camera and being moved to the second position to bring the second specimen within the field of view of the camera. In a further example, the at least one characteristic of the plurality of test specimens is a transformation temperature.

In yet another exemplary embodiment of the present disclosure, an apparatus for testing at least one characteristic of a plurality of test specimens is provided. The plurality of test specimens being shape memory alloys. The apparatus comprising a chiller unit having a tank with liquid medium therein. The chiller unit including a cooling unit which is configured to lower a temperature of the liquid medium and a heating unit which is configured to raise the temperature of the liquid medium. The apparatus further comprising a removable fixture having a plurality of stations. Each station being capable of holding at least one test specimen. The removable fixture being positionable within the tank of the chiller unit such that the at least one test specimen is submerged in the liquid medium. The apparatus further comprising a camera positioned above the tank and having a field of view directed at a top side of the fixture; a rotational base coupled to the camera and configured to move the camera to position the field of view of the camera sequentially at each station which is holding at least one test specimen, the camera capturing at least one image of the test specimen at each station; and an electronic controller operatively coupled to the chiller unit to control the temperature of the liquid medium, operatively coupled to the rotational base to position the field of view of the camera, and operatively coupled to the camera to receive information regarding each test specimen. In one example, each of the plurality of stations of the removable fixture has a test specimen held thereby, a first end of each test specimen being held by the removable fixture and a second end of each test specimen being unsupported and able to move relative to the first end. In another example, a first number of the plurality of stations of the removable fixture has a test specimen held thereby. The first number being less than all of the plurality of stations. The electronic controller receiving at least one input which indicates the first number of stations and the electronic controller instructing the rotational base to move past stations not included in the first number of stations. In a further example, the electronic controller is operatively coupled to the camera through a wireless connection. In still another example, the test specimens include at least two groups, a first group having a first diameter and a second group having a second diameter. The first group and the second group being held by the removable fixture at the same time.

In yet a further exemplary embodiment of the present disclosure, a fixture for holding a plurality of test specimens is provided. The fixture comprising a base member; a central hub having a plurality of holders each of which holds a first end of a respective test specimen; and a plurality of mandrels spaced-apart from the central hub, each of the plurality of mandrels having a profile about which a respective test specimen may be shaped. In one example, the plurality of holders are radial openings in the central hub. In another example, the plurality of mandrels are removably coupled to the base member. In a further example, the central hub is removably coupled to the base member. In still a further example, the fixture further comprises a handle extending above the plurality of holders of the central hub. In yet another example, a second end of each of the plurality of test specimens is unsupported. In still another example, a center of each of the mandrels is equally spaced from a center of the base member of the fixture. In yet still another example, a center of a first mandrel is equidistant from two adjacent mandrels.

In a further exemplary embodiment of the present disclosure, a test apparatus and method for the determination of transformation temperatures of shape memory metal alloys are provided. In one embodiment, the test apparatus is designed to very accurately implement ASTM Standard F2082, and generally includes a chiller unit including a tank containing a chilling medium, such as isopropyl alcohol or denatured alcohol, which holds a removable fixture tray that can accommodate up to ten specimens, or more. The fixture tray holds the test specimens in an initial deformed condition, and the cooling medium may be gradually heated to induce transformation of the specimens. A vision-based optical system includes a camera which tracks the specimens within its field of view, and associated software operates with the camera to detect and plot shape changes of the specimens versus temperature to very accurately determine transformation temperatures of the specimens.

In still another exemplary embodiment of the present disclosure, a test apparatus for determining a transition temperature of a shape memory metal alloy is provided. The test apparatus including a temperature control device including a container with a liquid medium; a specimen holding member removably positionable in the container, the specimen holding member capable of holding a plurality of test specimens; a camera system including a camera having a field of view encompassing at least one test specimen of the specimen holding member; and a software program controlling the temperature control device and the camera system, the software program concurrently measuring temperature changes and shape changes of the specimens to determine a transition temperature of at least one of the specimens.

In yet another exemplary embodiment of the present disclosure, a method for testing at least one characteristic of a plurality of test specimens is provided. The method comprising the steps of: supporting the plurality of test specimens on a fixture in a spaced apart relationship; setting an environmental characteristic of a region surrounding the plurality of test specimens to a first value; capturing at least one image of each of the plurality of test specimens at the first value of the environmental characteristic of the region surrounding the plurality of test specimens; changing the environmental characteristic of the region surrounding the plurality of test specimens to a second value; capturing at least one image of each of the plurality of test specimens at the second value of the environmental characteristic of the region surrounding the plurality of test specimens; and determining the at least one characteristic of the plurality of test specimens based on the images of the plurality of test specimens at the first value of the environmental characteristic of the region surrounding the plurality of test specimens and the second value of the environmental characteristic of the region surrounding the plurality of test specimens.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Figure 1:
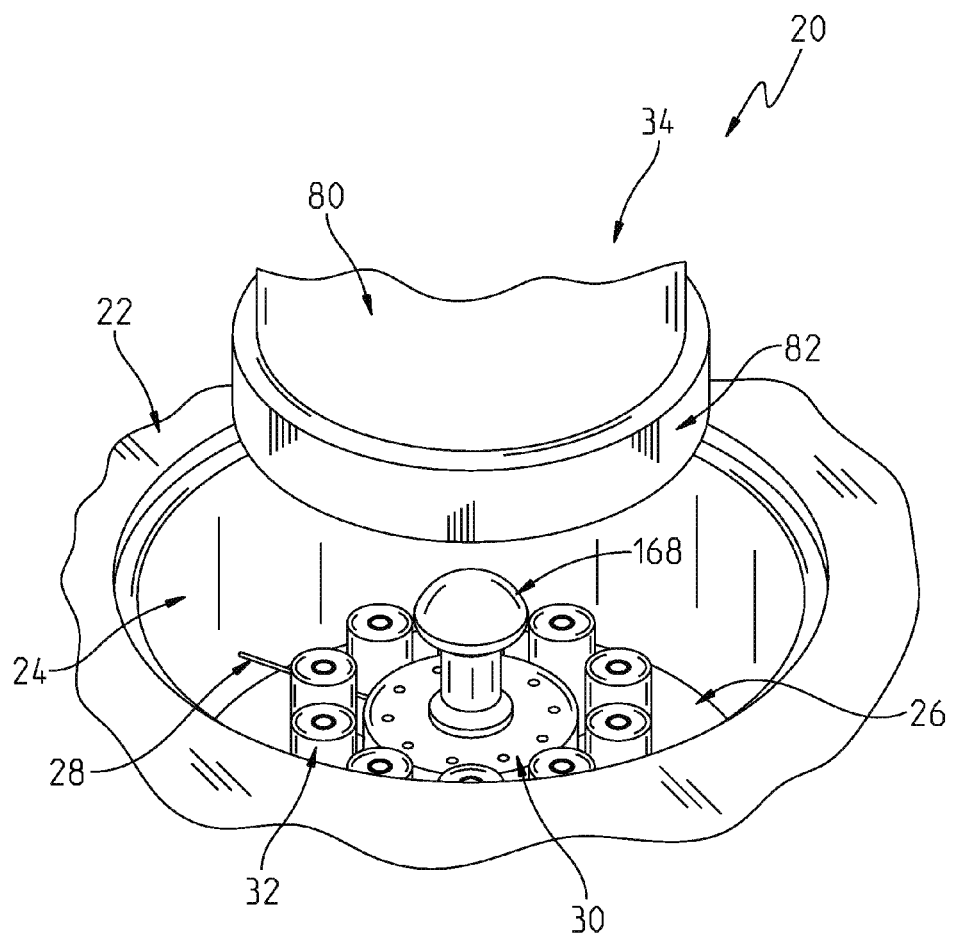
FIG. 1 illustrates a portion of a test apparatus, including the chiller unit, the tank, and the fixture tray.

The exemplification set out herein illustrates one embodiment of the invention, and such exemplification is not to be construed as limiting the scope of the invention in any manner.

DETAILED DESCRIPTION OF THE DRAWINGS

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides a test apparatus and method for the determination of at least one characteristic of a plurality of test specimens. In one embodiment, an environmental characteristic of a region surrounding the plurality of test specimens is changed over time. An exemplary environmental characteristic is temperature. An exemplary test specimen is a shape memory alloy and an exemplary characteristic is a transformation temperature of the shape memory alloy. Other exemplary characteristics may also be monitored.

In one embodiment, the test apparatus is designed to very accurately implement ASTM Standard F2082, and generally includes a chiller unit including a tank containing a chilling medium. An exemplary chilling medium is isopropyl alcohol. Another exemplary chilling medium is denatured alcohol. The test specimens are supported on a removable fixture tray. In one embodiment, the fixture tray may hold up to ten test specimens. Of course, the fixture tray may be configured to hold more or less test specimens. In one embodiment, the test specimens are wires having a diameter in the range of about 0.002 inches to about 0.040 inches.

In the case of determining a transition temperature of a shape memory alloy, the fixture tray holds the test specimens in an initial deformed condition and the cooling medium is gradually heated to induce transformation of the test specimens. A vision-based optical system includes a camera which tracks the test specimens within its field of view, and associated software executed by an electronic controller determines the transformation temperatures of the test specimens. The electronic controller communicates with the chiller to control the temperature of the liquid chilling medium and communicates with the camera to receive information regarding the shape of the test specimens. The electronic controller operates with the camera to detect and plot shape changes of the test specimens versus temperature to very accurately determine transformation temperatures of the specimens.

The present apparatus has several distinct advantages over the known apparatuses described in the Background section above. In one embodiment, the present test apparatus utilizes machine vision to accurately measure displacement of the test specimens without physical contact with the specimens. In one embodiment, the present apparatus also makes use of a two-stage chiller unit to cool the bath to the appropriate temperature, and may continually and accurately adjust the bath temperature throughout the test cycle to adhere to the ASTM Standard F2082 specifications. In one embodiment, the present apparatus may also simultaneously test ten or more specimens.

Referring to FIG. 1, a portion of a test apparatus 20 is shown. Test apparatus 20 includes an exemplary temperature control device, shown as a chiller unit 22, which includes a tank 24 that contains a liquid medium 23. An exemplary liquid medium 23 is isopropyl alcohol. Another exemplary liquid medium is denatured alcohol. Tank 24 also contains a specimen holding member, shown as a removable fixture tray 26. The fixture tray 26 may hold up to ten wire test specimens 28. The wire specimens 28 are held by a center hub 30 of fixture tray 26 and are bent around outer mandrels 32 once in the martensitic state. The ASTM Standard F2082 calls for an outer fiber strain of 2-2.5%, which is 39-49 times the wire diameter. The individual mandrels 32 are interchangeable to include different size mandrels, providing the ability to test specimens of various diameters.

Figure 2:
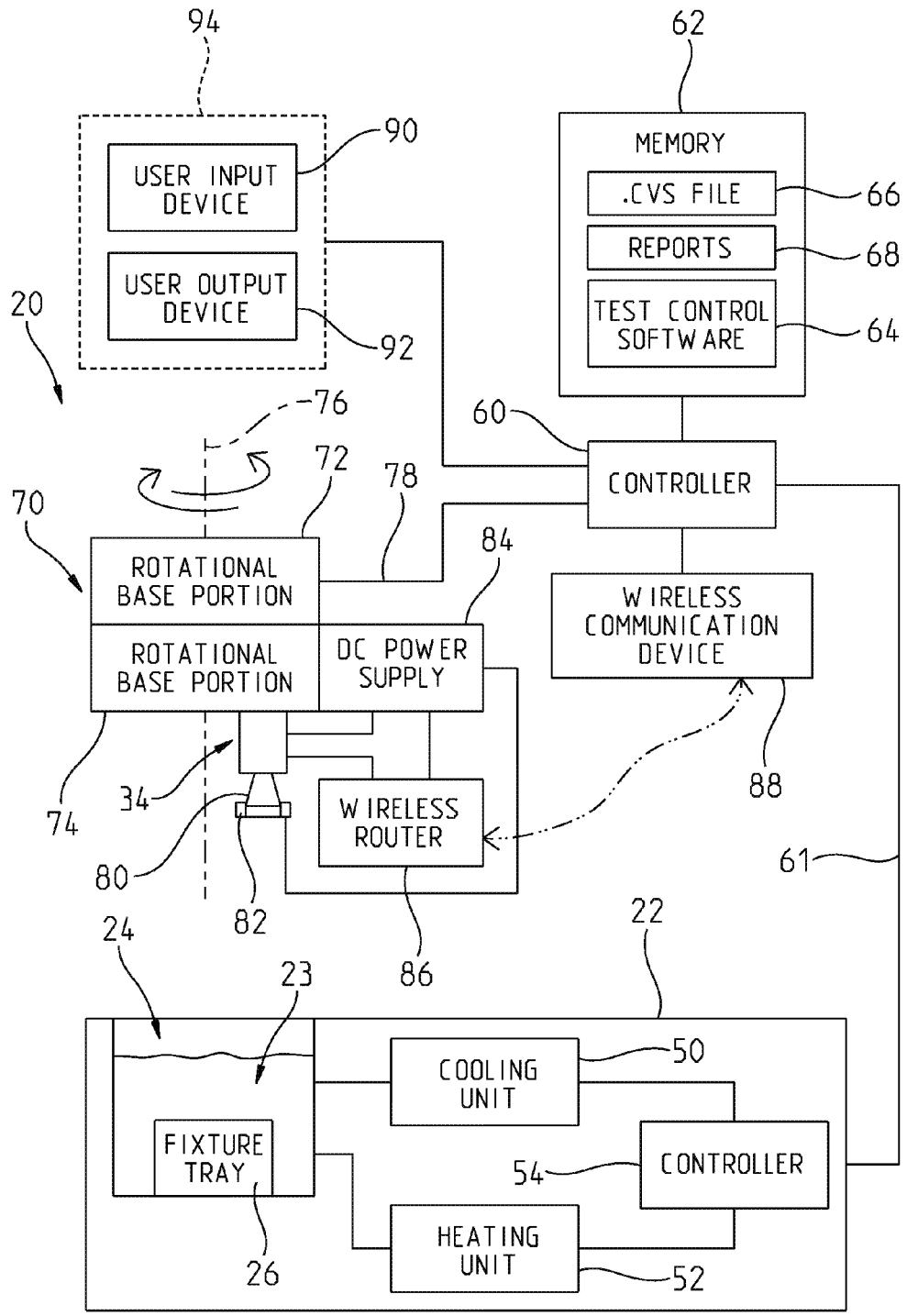
FIG. 2 illustrates a representative view of the test apparatus of FIG. 1.

Referring to FIG. 2, a representative view of test apparatus 20 is shown. Chiller unit 22 includes a cooling unit 50 which interacts with liquid medium 23 to lower a temperature of liquid medium 23 and a heating unit 52 which interacts with liquid medium 23 to raise a temperature of liquid medium 23. In one embodiment, a magnetic stirrer or other device is provided in a bottom portion of tank 24 to assist in keeping the temperature of the bath at a uniform temperature. The operation of cooling unit 50 and heating unit 52 is controlled by an electronic controller 54. An exemplary chiller unit 22 is model MC880, available from FTS of Stone Ridge, N.Y. In one embodiment, cooling unit 50 is a two stage compressor which can lower the temperature of liquid medium 23 to a minimum of −80° C. in tank 24. The electronic controller 54 uses heating unit 52 to raise a temperature of liquid medium 23. In one embodiment, the temperature of liquid medium 23 is raised by electronic controller 54 at a rate no greater than 4° C./min.

In one embodiment, electronic controller 54 receives instructions on the desired temperature of liquid medium 23 from an electronic controller 60 of test apparatus 20. Exemplary electronic controllers include personal computers and other suitable electronic devices which may be programmed to execute software. Although electronic controller 60 is illustrated as a single controller, it should be understood that multiple computing systems may be used together, such as over a network or other methods of transferring data. In one embodiment, electronic controller 60 is coupled to electronic controller 54 through a wired serial connection 61. Other wired or wireless connections may be made between electronic controller 54 and electronic controller 60 as opposed to or in addition to wired serial connection 61.

Electronic controller 60 has access to a memory 62 which includes test control software 64, data files 66, and report files 68. Electronic controller 60 executes test control software 64 stored on memory 62. Memory 62 is a computer readable medium and may be a single storage device or may include multiple storage devices, located either locally with electronic controller 60 or accessible across a network. Computer-readable media may be any available media that may be accessed by electronic controller 60 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by computing system 100.

Memory 62 includes operating system software (not shown). An exemplary operating system software is a WINDOWS operating system available from Microsoft Corporation of Redmond, Wash. Memory 62 further includes communications software (not shown) which controls the communication between electronic controller 60 and electronic controller 54 and between electronic controller 60 and other devices.

As stated herein, memory 62 includes test control software 64. Although described as software, it is understood that at least portions of test control software 64 may be implemented as hardware. As explained herein, test control software 64 based on a plurality of inputs determines at least one characteristic of a plurality of test specimens 28.

Electronic controller 60 is further coupled to a rotational base 70. Rotational base 70 includes a first stationary portion 72 and a second movable portion 74. Second movable portion 74 is rotatable about an axis 76 relative to second movable portion 74. Axis 76 is vertical and generally normal to a top surface of a base member 150 (see FIG. 4) of fixture tray 26. In one embodiment, rotational base 70 is a rotary servo table, such as model ADRS200, available from Aerotech, Inc. of Pittsburgh, Pa. Electronic controller 60 is connected to rotational base 70 through a wired serial connection 78. Electronic controller 60 controls the angular position of second movable portion 74 relative to first stationary portion 72 through wired serial connection 78. Other wired or wireless connections may be made between rotational base 70 and electronic controller 60 as opposed to or in addition to wired serial connection 78.

A camera 34 is coupled to rotational base 70. An exemplary camera is model T27, available from PPT Vision, Inc. of Eden Praire, Minn. Camera 34 is oriented to image at least a portion of fixture tray 26 when positioned in tank 24. Camera 34 includes a lens system 80 which may be adjusted to vary a field of view of camera 34. A light ring 82 is mounted to a front of lens system 80 and illuminates at least the portion of fixture tray 26 being imaged by camera 34.

Both camera 34 and light ring 82 receive power from a DC power supply 84. In one embodiment, DC power supply 84 is mounted to rotational base 70. Rotational base 70 is also powered by DC power supply 84. In one embodiment, AC power is fed via slip rings to the DC power supply 84 when DC power supply 84 is mounted to second movable portion 74. Camera 34 communicates with electronic controller 60 through a wireless router 86 which communicates with a wireless communication device 88 accessible by electronic controller 60. In one embodiment, electronic controller 60 and camera 34 communicate via wireless Ethernet.

Electronic controller 60 also is coupled to at least one user input device 90. Exemplary user input devices 90 include buttons, knobs, keys, switches, a mouse, a roller ball, and other suitable devices for providing an input to electronic controller 60. Electronic controller 60 is further coupled to at least one user output devices 92. Exemplary user output devices include display screens, printers, lights, and other suitable devices for providing an output from electronic controller 60. In one embodiment, user input device 90 and user output device 92 are combined into a single user interface device 94. An exemplary user interface device 94 is a touch screen interface. In one embodiment, electronic controller 60 and single user interface device 94 are shown as a panel PC 98 (see FIG. 3).

Figure 3:
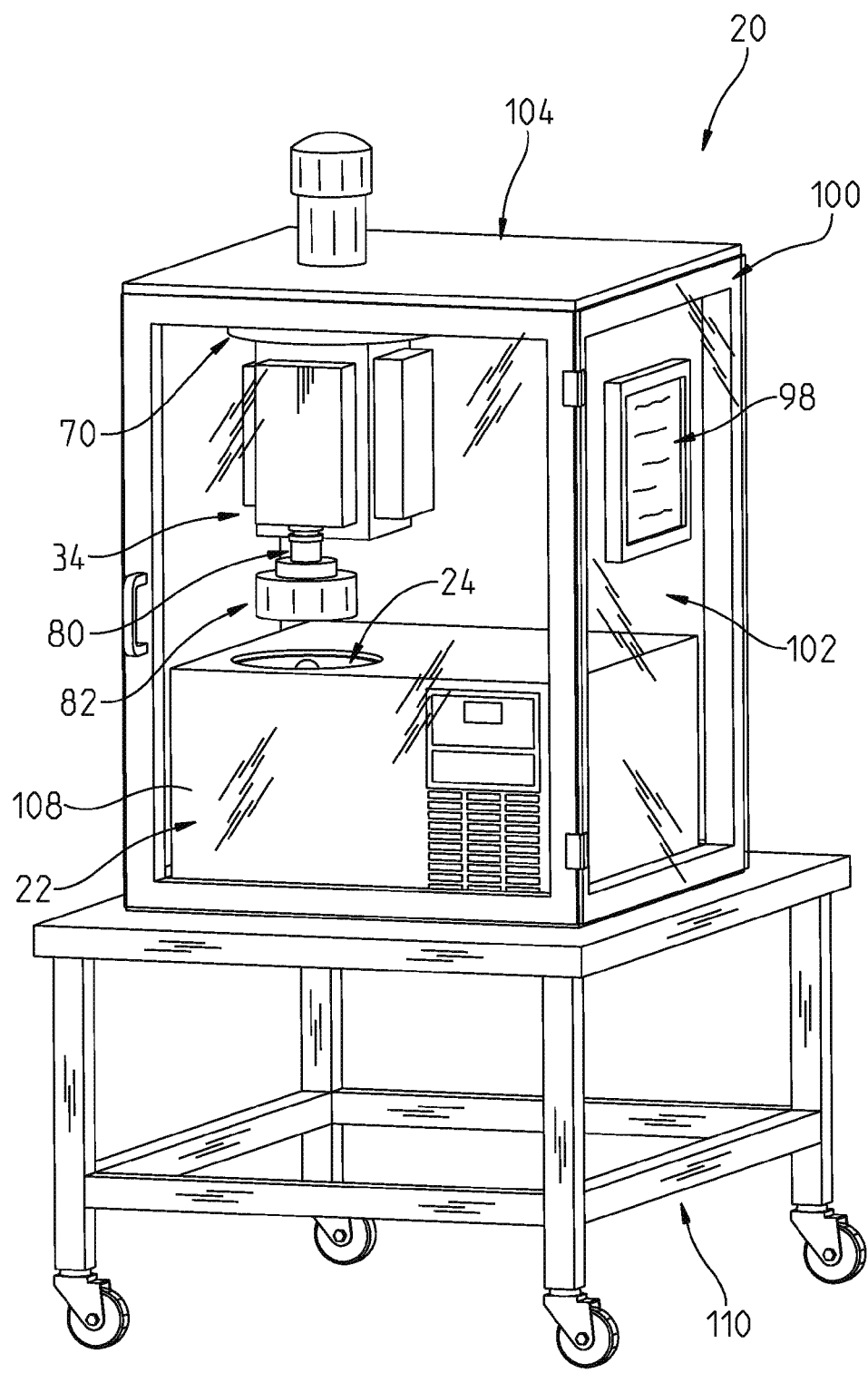
FIG. 3 illustrates the test apparatus of FIG. 1 positioned on a moveable cart.

Referring to FIG. 3, test apparatus 20 includes a frame 100 which supports rotational base 70. Frame 100 also supports a plurality of side walls 102 and a roof 104. The plurality of side walls 102 and roof 104 form an enclosure 106 in which chiller unit 22 is positioned. Enclosure 106 includes a door 108 which permits ingress and egress relative to an interior of enclosure 106, such as tank 24 of chiller unit 22. Enclosure 106 is shown supported on a moveable cart 110 which permits test apparatus 20 to be transported from place to place as desired.

Figure 4:
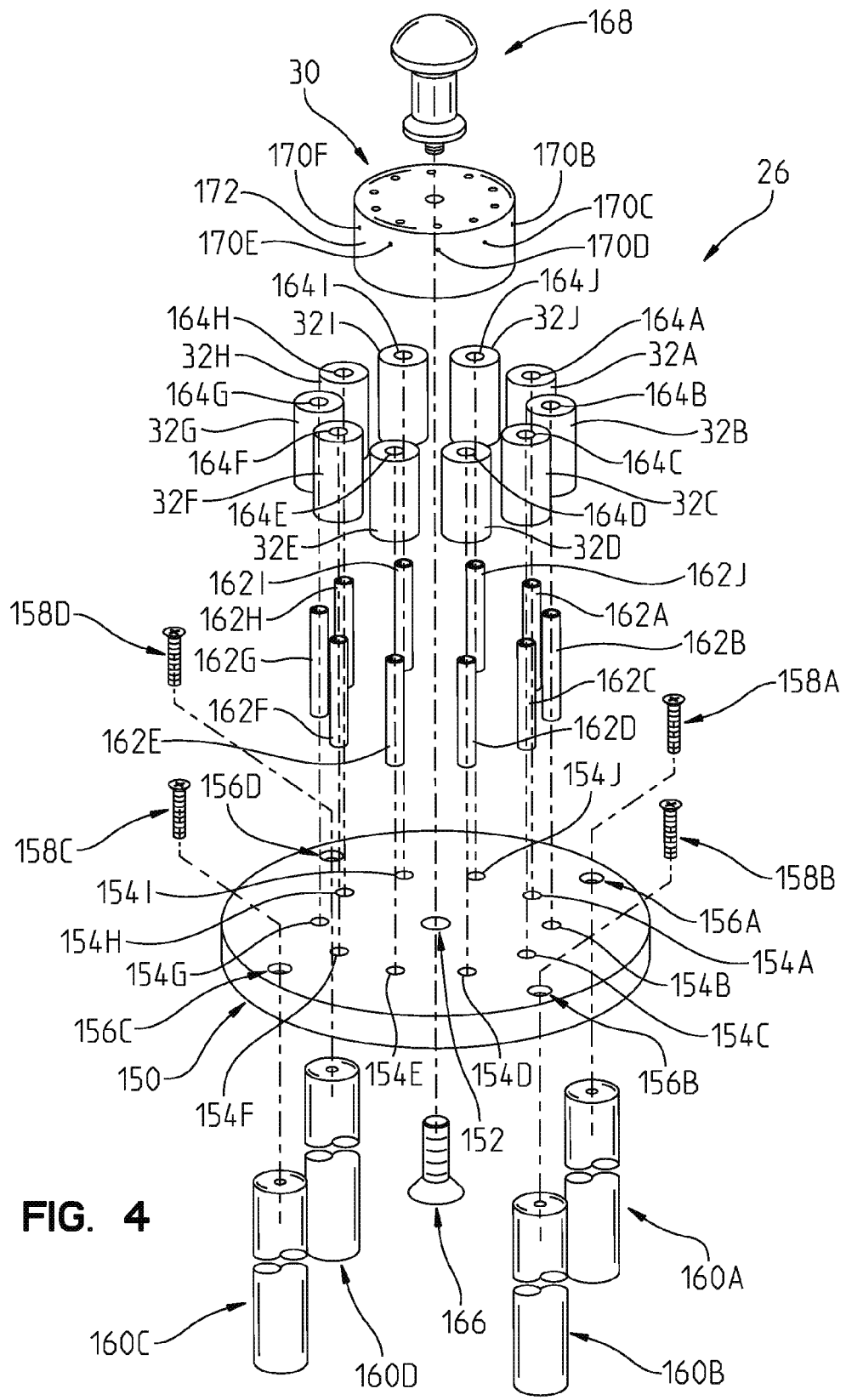
FIG. 4 illustrates an exploded view of an exemplary fixture tray.

Referring to FIG. 4, an exemplary embodiment of fixture tray 26 is shown. Fixture tray 26 includes a base member 150. Base member 150 is shown as a circular plate having a central opening 152, a plurality of openings 154 which will position outer mandrels 32, and a plurality of openings 156. Openings 156 receive couplers 158 which couple to leg members 160. Leg members 160 support base member 150 off of a bottom of tank 24. In one embodiment, fixture tray 26 is made of a non-metallic material. Exemplary materials include materials with low specific heat capacity, such as ultra-high molecular weight (UHMW) plastic.

Figure 5:
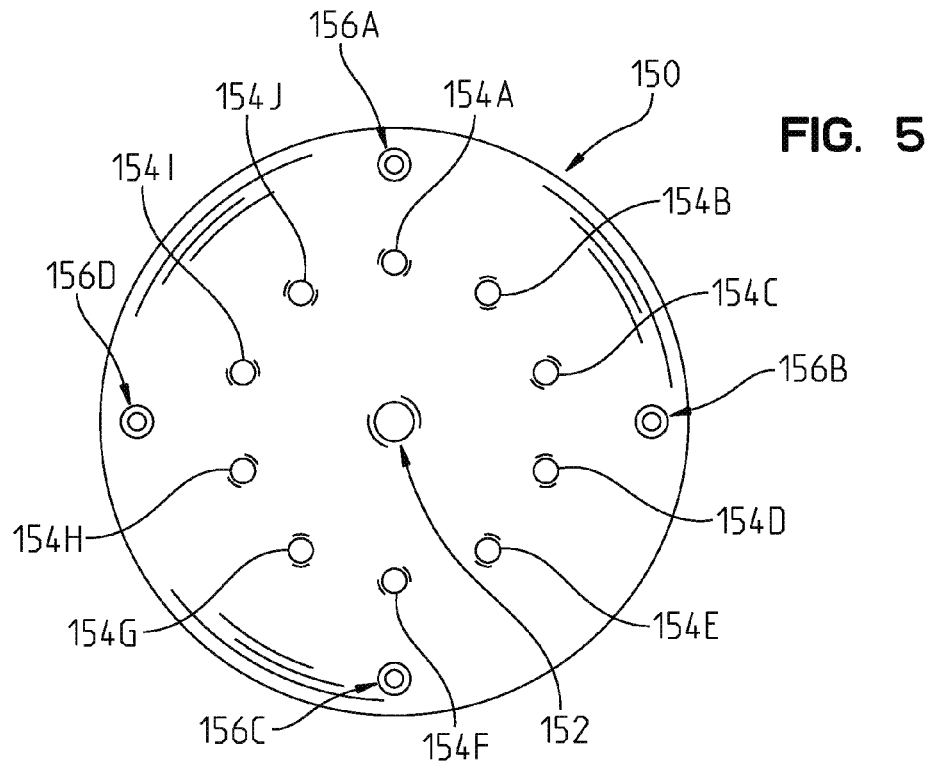
FIG. 5 illustrates a top view of a base member of the fixture tray of FIG. 4.

Referring to FIG. 5, openings 154 are each an equal distance from central opening 152 and are equally spaced relative to each other. In the illustrated embodiment, openings 154 are arranged such that each of openings 154 are separated by 36 degrees. In one embodiment, the spacing of openings 154 is not constant.

Returning to FIG. 4, pins 162 are received in openings 154. Pins 162 also are received in corresponding openings 164 in outer mandrels 32. In one embodiment, pins 162 are press fit into openings 164 of outer mandrels 32 and removably received in openings 154 of base member 150. In one embodiment, pins 162 are press fit into openings 154 of base member 150 and are removably received in openings 164 of outer mandrels 32. In either case outer mandrels 32 are removably coupled to openings 156.

Figure 6:
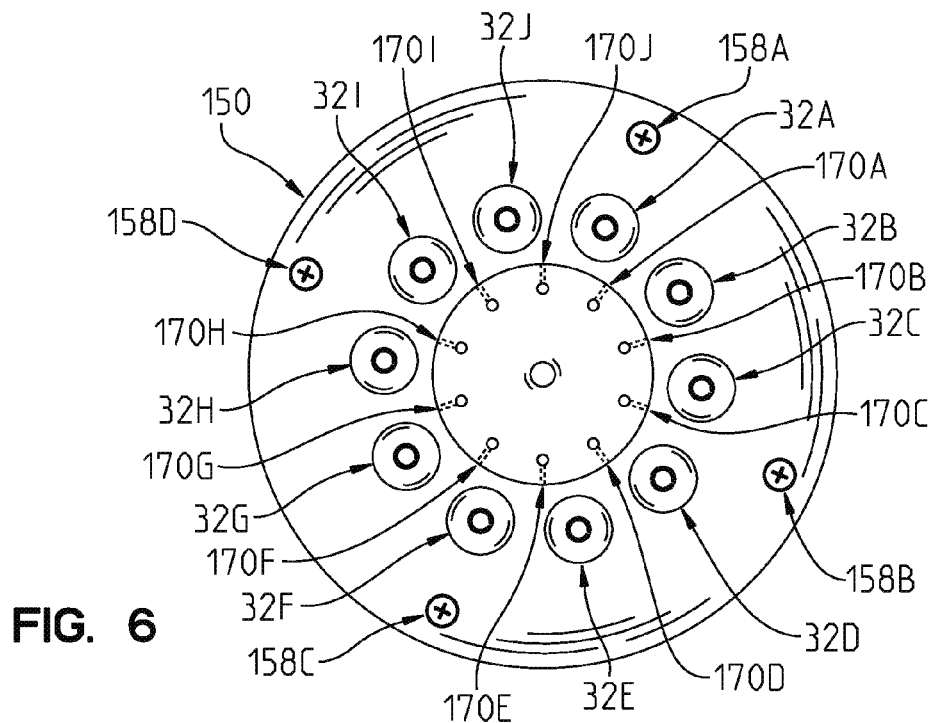
FIG. 6 illustrates the top view of the base member of FIG. 5 with a center hub coupled thereto and a plurality of mandrels.

Center hub 30 is coupled to openings 156 through a coupler 166 which is threaded into an underside of center hub 30. A handle 168 is coupled to a top portion of center hub 30. Handle 168 provides an operator with an easy way to lift fixture tray 26 out of tank 24 and to place fixture tray 26 within tank 24. Center hub 30 includes a plurality of radial openings 170 provided in a side wall 172 (see FIG. 4) of center hub 30. Referring to FIG. 6, there is one radial opening 170 for each outer mandrel 32. Further, radial openings 170 are positioned such that a test specimen 28 extending straight radially outward from a respective radial opening 170 is positioned along a first side of the corresponding outer mandrel 32. In one embodiment, fixture tray 26 is keyed relative to tank 24 so that fixture tray 26 may be repeatably positioned within tank 26.

Figure 7:
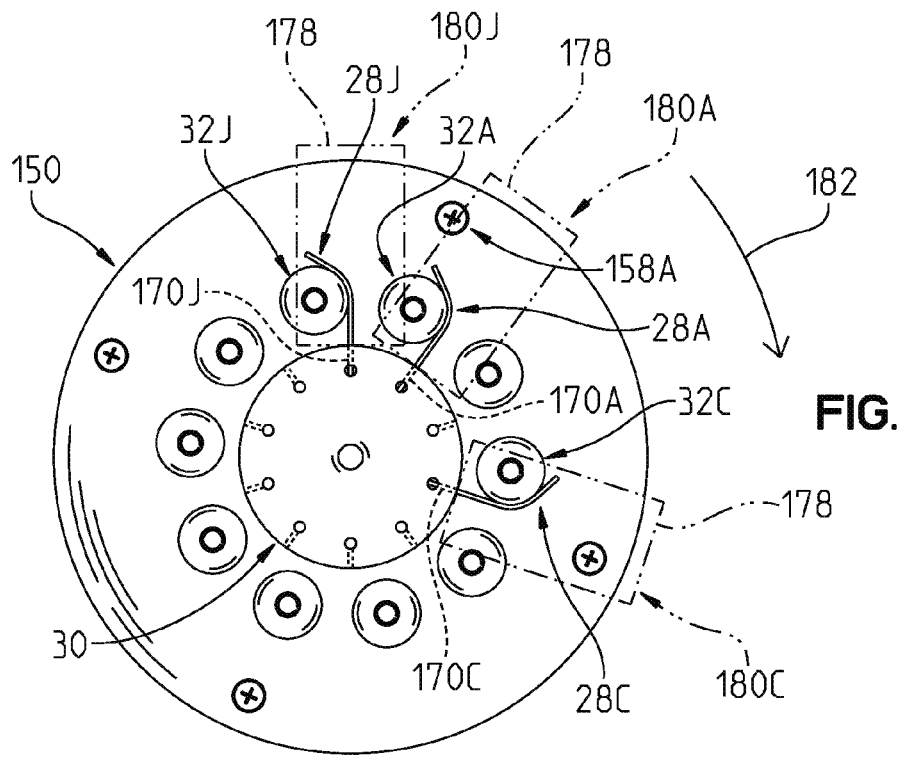
FIG. 7 illustrates the top view of FIG. 6 with a plurality of test specimens coupled to the center hub and bent relative to respective mandrels.

Referring to FIG. 7, three wire specimens, 28A, 28C, and 28J, are coupled to fixture tray 26. Each of wire specimens 28A, 28C, and 28J are shown having a first end received in their respective radial opening 170A, 170C, and 170J of center hub 30 and a second end bent relative to their respective mandrel 32A, 32B, and 32J. In the illustrated embodiment of FIG. 7, each of outer mandrels 32 are the same size. In one embodiment, outer mandrels 32 may be of differing size such that a first test specimen 28, such as wire specimen 28J, may be bent at a different radius than a second test specimen 28, such as wire specimen 28C.

Figure 8:
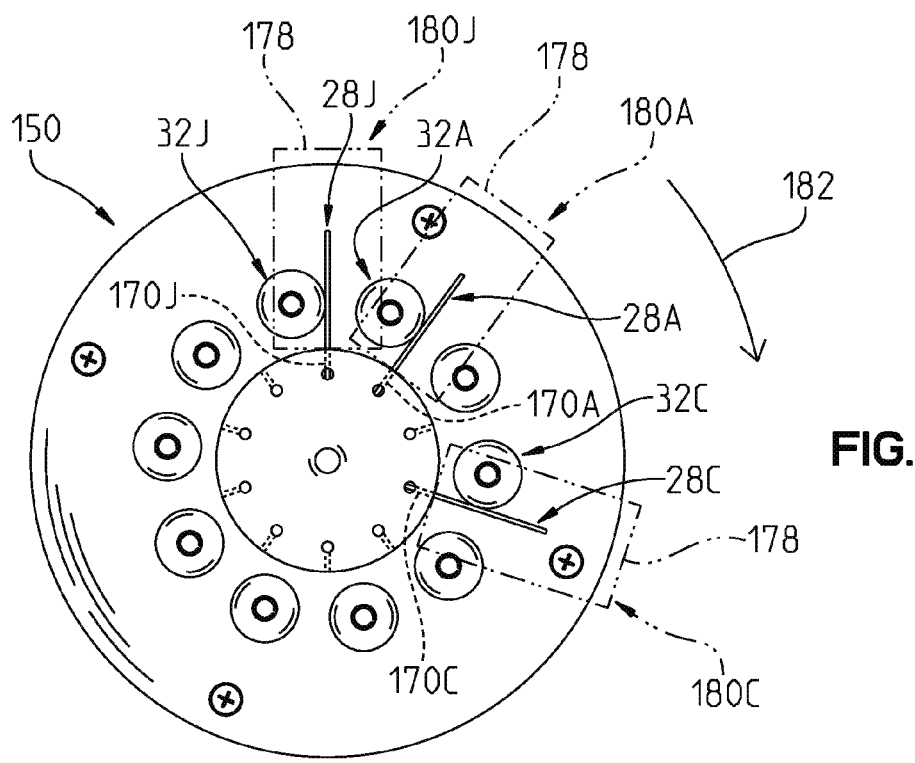
FIG. 8 illustrates the top view of FIG. 7 with the plurality of test specimens in a straight configuration.
Figure 11A:
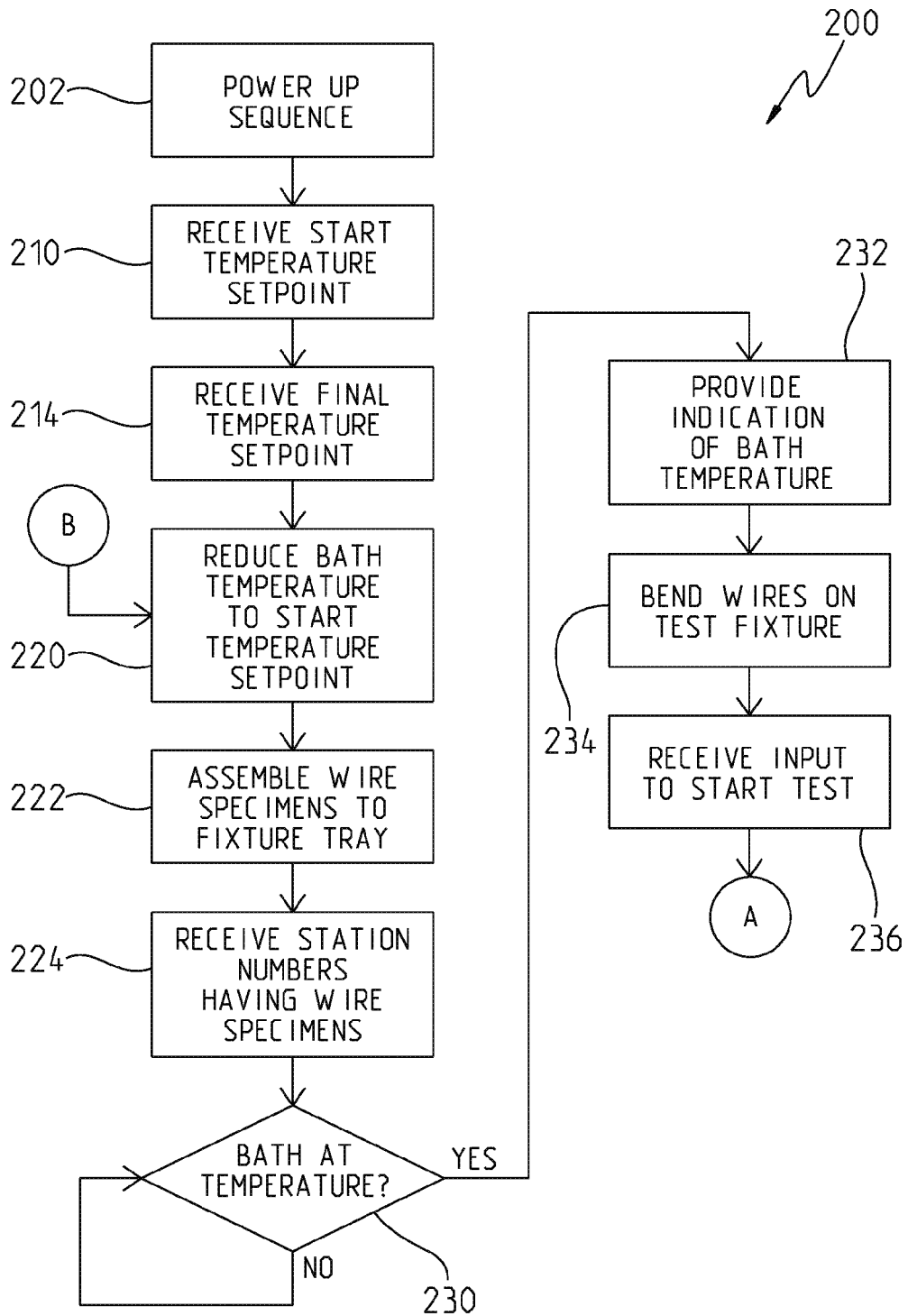
FIGS. 11A and 11B illustrate an exemplary test procedure for the test apparatus of FIG. 2.
Figure 11B:
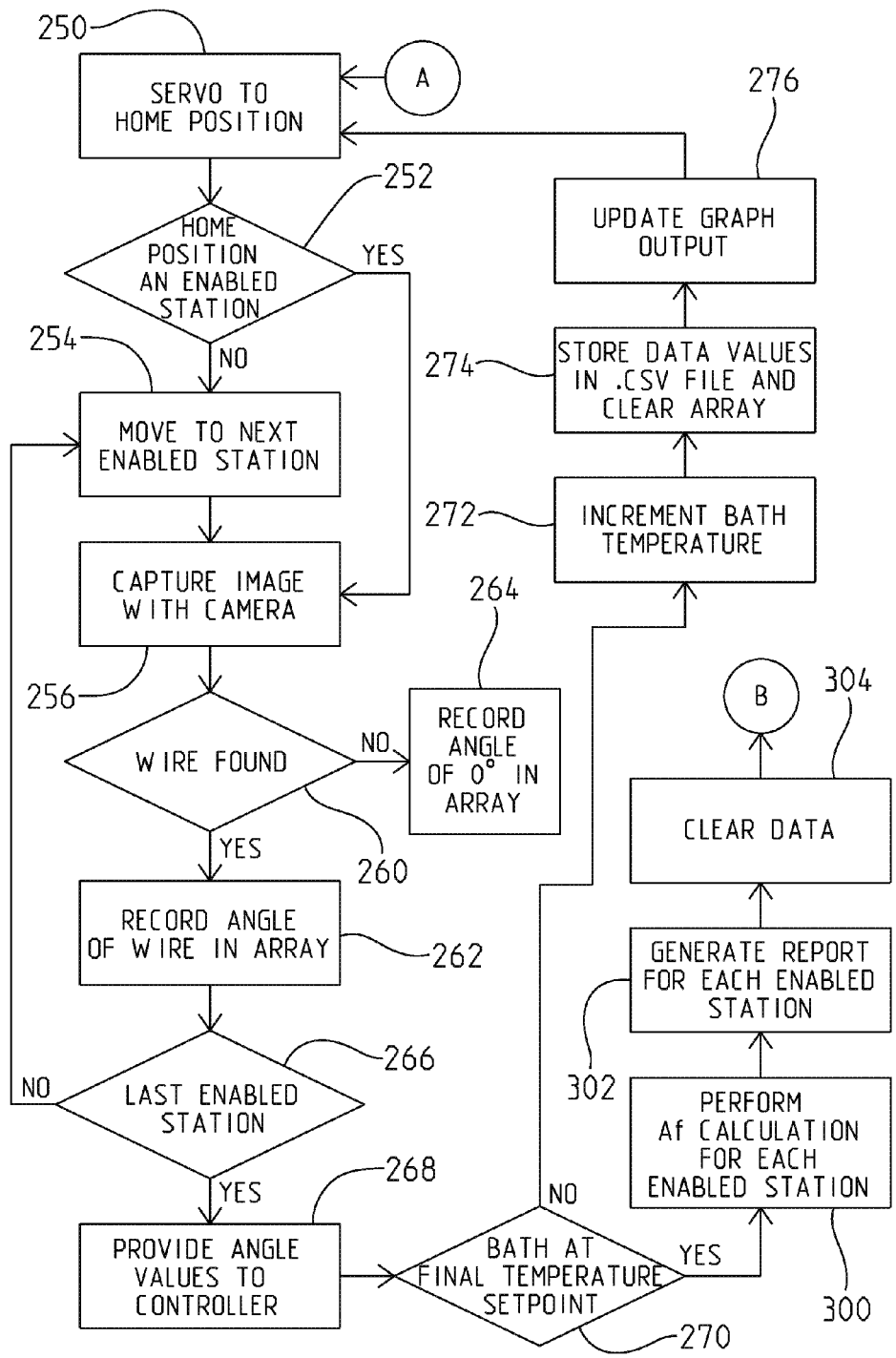

The bent shape of the test specimens 28 in FIG. 7 is the initial position of test specimens 28 during a testing procedure discussed in conjunction with FIGS. 11A and 11B to determine a transition temperature of test specimens 28. As a temperature of liquid medium 23 in tank 24 is raised, a temperature of test specimens 28 is also raised eventually causing test specimens 28 to straighten as shown in FIG. 8.

Returning to FIG. 7, a field of view 178 of camera 34 is shown. In the illustrated embodiment, field of view 178 is sized and positioned to image a single test specimen 28 at a time. The field of view 178 of the camera 34 may be made quite small due to lens choice, in order to provide a 4 pixel resolution for a 0.002" diameter test specimen 28. In one embodiment, field of view 178 is sized and positioned to image multiple test specimens 28 at a time. As illustrated in FIG. 7, field of view 178 is moved to image different test specimens 28. Each position of field of view 178 corresponds to a station 180 of test apparatus 20. In one embodiment, field of view 178 is moved by moving camera 34. Camera 34 is moved by indexing rotational base 70. In the illustrated example with ten stations 180, rotational base 70 indexes 36° to move from a current station 180 to an adjacent station 180. By moving camera 34 instead of fixture tray 26, the fluid flow relative to the test specimens 28 is minimized.

Figure 10:
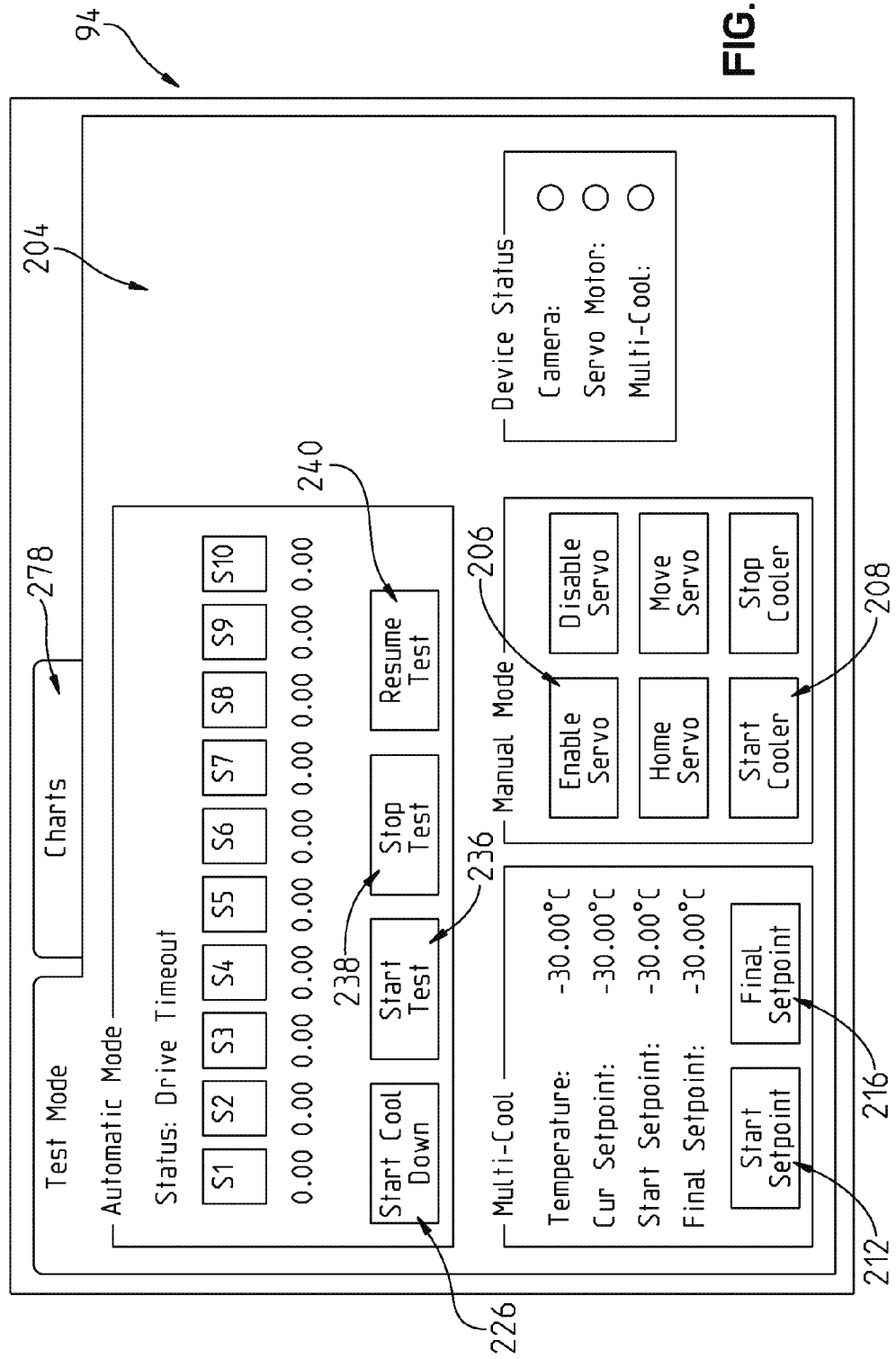
FIG. 10 illustrates a sample user interface of the test apparatus of FIG. 2.

Referring to FIGS. 11A and 11B an exemplary test procedure 200 is shown. If test apparatus 20 is not currently running, a power up sequence is performed, as represented by block 202. In one embodiment, during the power up sequence, electronic controller 60, chiller unit 22, camera 34 and rotational base 70 are initialized. An operator of test apparatus 20 then provides an input to enable the servos of rotational base 70 and to start chiller unit 22. Referring to FIG. 10, an exemplary screen 204 of a touch interface 94 is shown. With touch interface 94, an operator may touch soft button 206 which corresponds to instructing electronic controller 60 to enable the servos of rotational base 70. Further, an operator may touch soft button 208 which corresponds to instructing electronic controller 60 to start chiller unit 22.

Returning to FIG. 10, a start temperature setpoint is provided to electronic controller 60 for the test procedure, as represented by block 210. The start temperature setpoint corresponds to a temperature that liquid medium 23 should be at to begin the testing procedure. In one embodiment, the value of the start temperature setpoint is stored in memory 62. In one embodiment, an operator selects a start setpoint soft button 212 provided on touch interface 94 as shown in FIG. 10. Touch interface 94 then provides the operator with one or more inputs to adjust the value of the start temperature setpoint. This value is then stored in memory 62.

In addition, an end temperature setpoint is provided to electronic controller 60 for the test procedure, as represented by block 214. The end temperature setpoint corresponds to a temperature that liquid medium 23 should be at when the testing procedure is completed. In one embodiment, the value of the end temperature setpoint is stored in memory 62. In one embodiment, an operator selects an end setpoint soft button 216 provided on touch interface 94 as shown in FIG. 10. Touch interface 94 then provides the operator with one or more inputs to adjust the value of the end temperature setpoint. This value is then stored in memory 62.

Once the start temperature setpoint and the end temperature setpoint have been received, electronic controller 60 controls chiller unit 22 to reduce the temperature of liquid medium 23 to the start temperature setpoint value, as represented by block 220. In one embodiment, electronic controller 60 instructs the chiller unit 22 to begin the cool down in response to soft touch button 226 (see FIG. 10) of touch interface 94 being selected. An operator also assembles wire test specimens 28 to fixture tray 26, as represented by block 222. The operator may couple a single wire test specimen 28 to one of radial openings 170 of fixture tray 26 up to a wire test specimen 28 to each of radial openings 170 of fixture tray 26.

The operator provides an input to electronic controller 60 of which stations 180 have wire specimens coupled thereto, as represented by block 224. In this manner, electronic controller 60 when it instructs rotational base 70 to move camera 34, it has rotational base 70 skip unused stations 180. In one embodiment, the input regarding enabled stations 180 is provided through screen 204 of touch interface 94. As shown, in FIG. 10, ten soft buttons labeled S1-S10 correspond to the ten stations 180. The operator enables a given station 180 by pressing the corresponding soft button. When selected to enable the station 180, the soft button changes state. In one embodiment, the soft button changes state by changing its displayed color to green. In one embodiment, the operator also enters an order number or other identifying information for the specimen of a given station 180. Once test specimens 28 are assembled to fixture tray 26, fixture tray 26 is placed in tank 24 such that test specimens 28 are submerged within liquid medium 23.

Chiller unit 22 provides an input to electronic controller 60 when liquid medium 23 has reached the start temperature setpoint, as represented by block 230. Electronic controller 60 provides an indication to the operator that the start temperature setpoint has been reached, as represented by block 232. In one embodiment, the indication is a message of 'Cool Down Complete' is displayed with touch interface 94. Other exemplary indications include audio indications, visual indications, tactile indications, and combinations thereof.

The operator then bends each of test specimens 28 relative to their respective outer mandrels 32, as represented by block 234. Once all of the test specimens 28 are properly bent, the operator provides an input to electronic controller 60 to begin the testing procedure, as represented by block 236. In one embodiment, the input is provided to electronic controller 60 by the selection of a soft touch button 236 (see FIG. 10) of touch interface 94 being selected. At anytime during testing, the operator may stop the test by selecting a soft button 238 of touch interface 94 and resume a test by selecting a soft button 240 of touch interface 94.

Electronic controller 60 moves rotational base 70 to a home position, if rotational base 70 is not already at the home position, as represented by block 250. In one embodiment, the home position is the zero angle position of rotational base 70. In one embodiment, the home position corresponds to station 180A. Electronic controller 60 based on the input provided by the operator determines if the home position corresponds to an enabled station 180, as represented by block 252. If not, electronic controller 60 through the control of rotational base 70 moves camera 34 to the first enabled station 180, as represented by block 254.

In one embodiment, camera 34 sends the images to electronic controller 60 for processing regarding the position of test specimens 28. In one embodiment, camera 34 includes a controller which executes software to analyze the position of the imaged test specimen 28. The image is processed by the controller of camera 34 to determine the presence of test specimens 28, as represented by block 260. If test specimen 28 is found in the image, then an angle of deflection for test specimens 28 is recorded in a table of a memory associated with the controller of camera 34, as represented by block 262. The angle of deflection is determined by detecting the free end of test specimens 28 and determining an angle that the free end of the test specimens 28 makes with the radial direction of radial openings 170 (the other end of test specimens 28). This value is recorded as the angle of deflection. An angle of deflection of 180° corresponds to test specimens 28 being straight, such as in FIG. 8. If the presence of test specimens 28 is not detected, a deflection angle value of 0° is recorded in the table, as represented by block 264. The angle of deflection is determined for each enabled station 180, as represented by block 266 and the return back to block 254. If at any time, rotational base 70 is unable to reach a given station 180, the servo of the rotational base 70 performs a homing routine wherein the rotational base 70 returns to the home position (0 degrees) and starts the testing over again. This eliminates the possibility of mixing station data during the test.

Once all of the enabled stations 180 have been imaged with camera 34, the table values corresponding to the angle of deflection for each station 180 is transmitted to electronic controller 60 via wireless router 86, as represented by block 268. Electronic controller 60 determines if liquid medium 23 is currently at the end setpoint temperature, as represented by block 270.

If not at the end setpoint temperature, electronic controller 60 instructs chiller unit 22 to raise the bath temperature to the next temperature, as represented by block 272. In one embodiment, the temperature of liquid medium 23 is changed in increments of about 1 degree between the start temperature setpoint and the end temperature setpoint. The angle of deflection values received from camera 34 are stored in data files 66 along with the temperature of the liquid medium 23 corresponding to the values, as represented by block 274. Further, electronic controller 60 updates the graph outputs for each enabled station, as represented by block 276. Electronic controller 60 then instructs camera 34 to determine the angle of deflection values for each enabled station 180 at the new temperature (once the bath is at the new temperature), as represented by the return to block 250.

Figure 9:
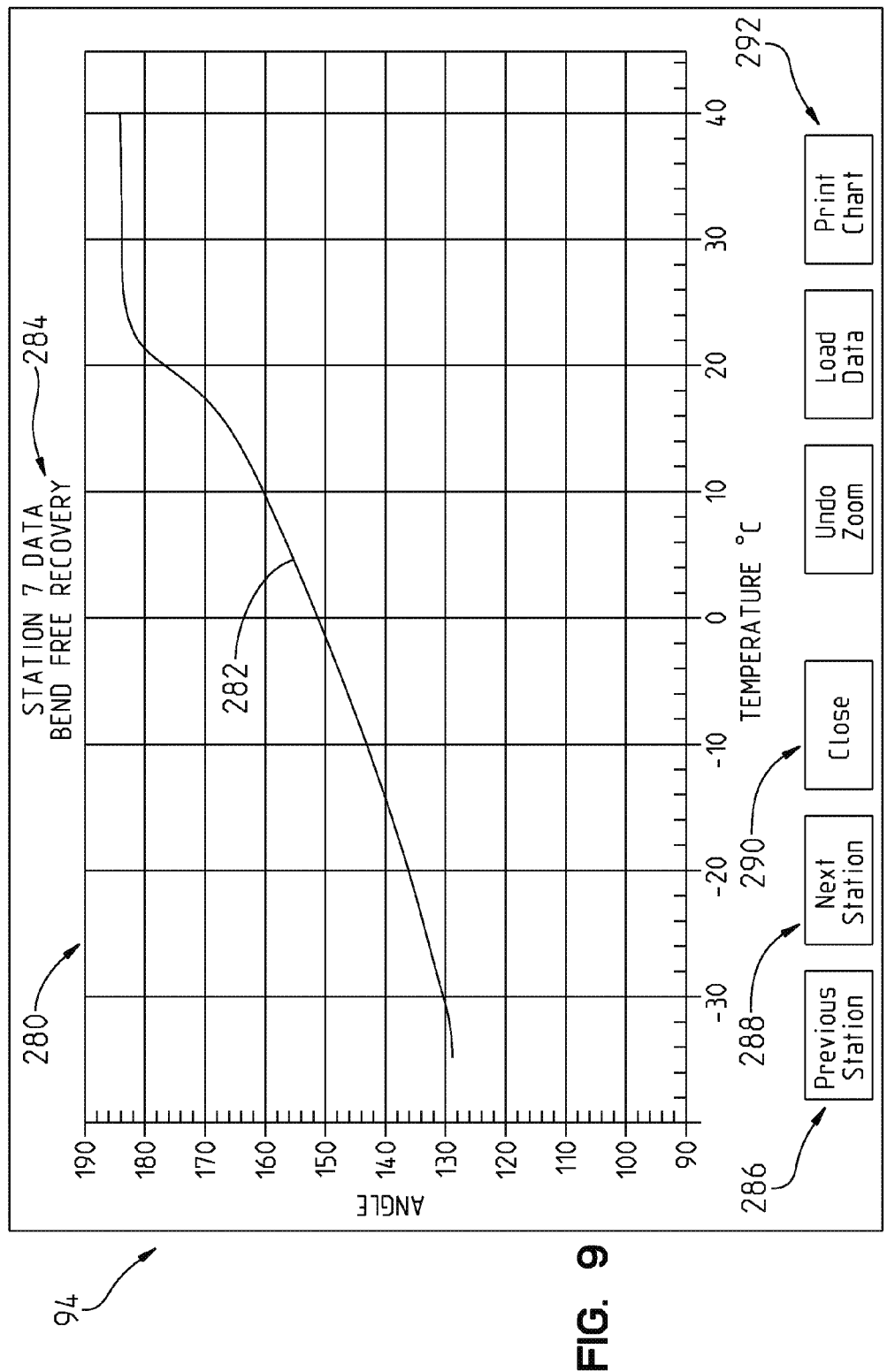
FIG. 9 illustrates a sample graph of the data obtained for a given test specimen, showing temperature vs. angle.

An exemplary graph 280 for a first enabled station 180 is shown in FIG. 9. Graph 280 may be selected through input 278 on touch interface 94. Graph 280 provides the angle of deflection for a given station 180 as a function of temperature, as represented by graph line 282. The station 180 being graphed is identified by textual label 284. An operator may select an earlier station 180 or a later station 180 through inputs 286 and 288 of touch interface 94, respectively. Further, an operator may close graph 280 by selecting input 290 of touch interface 94. The operator may send the chart to an accessible printer for printing by selecting input 292 of touch interface 94.

In one embodiment, the temperature of liquid medium 23 is changed in increments of 1 degree between the start temperature setpoint and the end temperature setpoint. The angle of deflection values received from camera 34 are stored in data files 66 along with the temperature of the liquid medium 23 corresponding to the values, as represented by block 274. Further, electronic controller 60 updates the graph outputs for each enabled station, as represented by block 276. Electronic controller 60 then instructs camera 34 to determine the angle of deflection values for each enabled station 180 at the new temperature (once the bath is at the new temperature), as represented by the return to block 250.

Returning to FIG. 11B, if the temperature of liquid medium 23 is at the end setpoint temperature, electronic controller 60 performs an Af calculation for each of test specimens 28, as represented by block 300. In one embodiment, the controller 60 utilizes regression analysis to identify two subsets of data. One subset represents the data collected while the specimen was moving (the sloped portion of the graph), the second is the data collected when the specimen was finished moving (the end more flat portion of the graph). A best fit line is then determined for each subset and the Af is determined as the intersection point of the two best fit lines. A report file 68 is generated for each enabled station 180, as represented by block 302. In one embodiment, the report file is a PDF document which includes a data table, a graph, a Af value, and order number. In one embodiment, the Af value is given to the nearest degree Centigrade. In one embodiment, the specification of the specimen, lot number and heat treatment are explicitly included. In one embodiment, the specification of the specimen, the lot number, and the heat treatment are specified or tied to the order number. The data stored in data files 66 is cleared, as represented by bock 304 and the temperature of liquid medium 23 is again reduced to start temperature setpoint to prepare for the next test procedure, as represented by the return to block 220. In one embodiment, data in data files 66 for each station is maintained until 'Start Test' button is pressed again in block 236.

Another exemplary test procedure includes the following steps:

Cool bath of chiller unit 22 to −55° C.;
Cut sample wire specimens 28 and place them in fixture tray 26;
Submerge fixture tray 26 into cooled bath;
Bend wire specimens 28 around mandrels 32 to achieve the 2-2.5% strain;
Close test set door and initiate test via PC 98 touchscreen;
The servo/camera system 34, 36 will find home position and begin indexing to each station, capturing image and transmitting data. With all 10 stations enabled it takes about 25 seconds to complete 1 rotation;
While the camera 34 continuously indexes, the bath is being warmed at the specified rate; and
When the bath reaches ending temperature (~30° C.), the test is terminated. Graphs and data for each station are prepared.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for testing at least one characteristic of a plurality of test specimens, the plurality of test specimens being shape memory alloys, the method comprising the steps of:
   supporting the plurality of test specimens on a fixture in spaced apart relationship;
   positioning the plurality of test specimens within a liquid bath;
   setting the temperature of the liquid bath at a first temperature;
   altering a shape of each of the plurality of test specimens while positioned in the liquid bath;
   capturing at least one image of each of the plurality of test specimens within the liquid bath when the liquid bath is at the first temperature;
   changing the temperature of the liquid bath to a second temperature;
   capturing at least one image of each of the plurality of test specimens within the liquid bath when the liquid bath is at the second temperature; and
   determining the at least one characteristic of the plurality of test specimens based on the images of the plurality of test specimens.

2. The method of claim 1, wherein the fixture includes a plurality of mandrels and the step of altering the shape of each of the plurality of test specimens while positioned in the liquid bath includes the step of bending each of the plurality of test specimens against a respective one of the plurality of mandrels.

3. The method of claim 1, further comprising the steps of:
   positioning a camera above the plurality of test specimens;
   while the liquid bath is at the first temperature, moving the camera such that each of the plurality of test specimens is within a field of view of the camera, the plurality of test specimens including a first test specimen and a second test specimen, the camera being moved to a first position to bring the first specimen within the field of view of the camera and being moved to a second position to bring the second specimen within the field of view of the camera; and
   while the liquid bath is at the second temperature, moving the camera such that each of the plurality of test specimens is within the field of view of the camera, the camera being moved to the first position to bring the first specimen within the field of view of the camera and being moved to the second position to bring the second specimen within the field of view of the camera.

4. The method of claim 3, wherein the camera captures at least a first image of the first test specimen when the camera is at the first position and the liquid bath is at the first temperature, at least a second image of the second test specimen when the camera is at the second position and the liquid bath is at the first temperature, at least a third image of the first test specimen when the camera is at the first position and the liquid bath is at the second temperature, and at least a fourth image of the second test specimen when the camera is at the second position and the liquid bath is at the second temperature.

5. The method of claim 4, further comprising the step of coupling the camera to a rotational base, the camera being moved by rotating the rotational base.

6. The method of claim 5, wherein a rotational axis of the rotational base is vertical.

7. The method of claim 1, wherein the at least one characteristic of the plurality of test specimens is a transformation temperature.

8. The method of claim 7, wherein the step of determining the at least one characteristic of the plurality of test specimens based on the images of the plurality of test specimens includes for each test specimen:
   imaging the test specimen at a plurality of temperatures, including the first temperature and the second temperature;
   locating the test specimen in each of the images;
   determining an angle of deflection made between a second end of the test specimen and a first end of the test specimen; and
   determining a transformation temperature of the test specimen based on the angle of deflection values of the test specimen at the plurality of temperatures.

9. The method of claim 8, wherein said step of imaging the test specimen at a plurality of temperatures comprises continuously imaging the test specimen while warming the temperature of the liquid bath at a specified rate.

10. The method of claim 7, wherein the transformation temperature comprises a martensite-to-austenite transformation temperature.

11. The method of claim 10, wherein the first temperature is −55° C. and the second temperature is 30° C.

12. The method of claim 1, wherein at least one of the plurality of test specimens comprises a nickel titanium alloy.

13. The method of claim 1, wherein the plurality of test specimens comprises a plurality of wires having respective diameters in the range of about 0.002 inches to about 0.040 inches.

14. The method of claim 1, wherein the plurality of test specimens are supported on a fixture such that each of the plurality of test specimens are equally spaced relative to each other.

15. The method of claim 1, wherein said step of setting the temperature of the liquid bath at a first temperature comprises providing a start temperature setpoint value to an electronic controller connected to a chiller unit, such that the chiller unit reduces the temperature of the liquid bath to the start temperature setpoint value.

16. The method of claim 15, wherein said step of changing the temperature of the liquid bath to a second temperature comprises providing an end temperature setpoint value to the electronic controller, such that the chiller unit raises the temperature of the liquid bath to the end temperature setpoint value.

17. The method of claim 16, wherein said step of capturing at least one image of each of the plurality of test specimens is repeated at regular incremental temperatures between the start temperature setpoint value and the end temperature setpoint value.

18. A method for testing at least one characteristic of a plurality of test specimens, the method comprising the steps of:
   supporting the plurality of test specimens on a fixture in spaced apart relationship;
   setting an environmental characteristic of a region surrounding the plurality of test specimens to a first value;
   capturing at least one image of each of the plurality of test specimens at the first value of the environmental characteristic of the region surrounding the plurality of test specimens;
   changing the environmental characteristic of the region surrounding the plurality of test specimens to a second value;
   capturing at least one image of each of the plurality of test specimens at the second value of the environmental characteristic of the region surrounding the plurality of test specimens; and
   determining the at least one characteristic of the plurality of test specimens based on the images of the plurality of test specimens at the first value of the environmental characteristic of the region surrounding the plurality of test specimens and the second value of the environmental characteristic of the region surrounding the plurality of test specimens.

19. The method of claim 18, wherein the fixture includes a plurality of mandrels and the method further includes the step of bending each of the plurality of test specimens against a respective one of the plurality of mandrels.

20. The method of claim 18, further comprising the steps of:
   positioning a camera above the plurality of test specimens;
   while the environmental characteristic of the region surrounding the plurality of test specimens is at the first value, moving the camera such that each of the plurality of test specimens is within a field of view of the camera, the plurality of test specimens including a first test specimen and a second test specimen, the camera being moved to a first position to bring the first specimen within the field of view of the camera and being moved to a second position to bring the second specimen within the field of view of the camera; and while the environmental characteristic of the region surrounding the plurality of test specimens is at the second value, moving the camera such that each of the plurality of test specimens is within the field of view of the camera, the camera being moved to the first position to bring the first specimen within the field of view of the camera and being moved to the second position to bring the second specimen within the field of view of the camera.

21. The method of claim 18, wherein at least one of the plurality of test specimens comprises a nickel titanium alloy.

22. The method of claim 18, wherein the plurality of test specimens comprises a plurality of wires having respective diameters in the range of about 0.002 inches to about 0.040 inches.

23. The method of claim 18, wherein said step of setting an environmental characteristic of a region surrounding the plurality of test specimens to a first value comprises:

setting a start temperature setpoint value using an electronic controller connected to a chiller unit, such that the chiller unit reduces the temperature of the region to the start temperature setpoint value.

24. The method of claim 23, wherein said step of changing the environmental characteristic of the region surrounding the plurality of test specimens to a second value comprises:

setting an end temperature setpoint value using the electronic controller, such that the chiller unit raises the temperature of the region to the end temperature setpoint value.

25. The method of claim 24, wherein the start temperature setpoint value is −55° C. and the end temperature setpoint value is 30° C.

26. The method of claim 18, wherein said step of capturing at least one image of each of the plurality of test specimens is repeated at regular increments between the first value and the second value of the environmental characteristic of the region surrounding the plurality of test specimens.

27. The method of claim 18, wherein the at least one characteristic of a plurality of test specimens comprises a martensite-to-austenite transformation temperature.

* * * * *